United States Patent
Kataoka et al.

(10) Patent No.: US 7,592,166 B2
(45) Date of Patent: *Sep. 22, 2009

(54) ENONE REDUCTASE GENE AND MICROBIAL PRODUCTION OF LEVODIONE

(75) Inventors: Michihiko Kataoka, Kyoto (JP); Sakayu Shimizu, Kyoto (JP)

(73) Assignee: DSM IP Assets B.V., TE Heerlen (NL)

( * ) Notice: Subject to any disclaimer, the term of this patent is extended or adjusted under 35 U.S.C. 154(b) by 317 days.

This patent is subject to a terminal disclaimer.

(21) Appl. No.: 10/528,960

(22) PCT Filed: Sep. 19, 2003

(86) PCT No.: PCT/EP03/10473

§ 371 (c)(1), (2), (4) Date: Oct. 31, 2005

(87) PCT Pub. No.: WO2004/027065

PCT Pub. Date: Apr. 1, 2004

(65) Prior Publication Data

US 2006/0128000 A1    Jun. 15, 2006

(30) Foreign Application Priority Data

Sep. 23, 2002  (EP) ................... 02021098

(51) Int. Cl.
- C12P 7/26 (2006.01)
- C12P 5/02 (2006.01)
- C12N 9/02 (2006.01)
- C12N 15/74 (2006.01)

(52) U.S. Cl. ............... 435/148; 435/167; 435/189; 435/252.3; 435/320.1

(58) Field of Classification Search .......... None
See application file for complete search history.

(56) References Cited

U.S. PATENT DOCUMENTS

| | | |
|---|---|---|
| 4,072,715 A | 2/1978 | Boguth et al. |
| 6,428,991 B1 | 8/2002 | Fukuoka et al. |

FOREIGN PATENT DOCUMENTS

| | | |
|---|---|---|
| EP | 1 236 796 | 9/2002 |
| WO | WO 03/070924 | 8/2003 |
| WO | WO 03/070959 | 8/2003 |

OTHER PUBLICATIONS

Vaz et al. (Biochem. 1995, 34, 4246-4256).*
Chica et al. (Curr Opin Biotechnol. Aug. 2005; 16(4):378-84).*
Seffernick et al. (J Bacteriol. Apr. 2001; 183 (8): 2405-10).*
Witkowski et al. (Biochemistry. Sep. 7, 1999; 38(36): 11643-50.*
Wanner and Tressl, "Purification and Characterization of Two Enone Reductases From *Saccharomyces cerevisiae*," *Eur. J. Biochem.*, vol. 255, pp. 271-278 (1998).
Kataoka, M. et al., "Old Yellow Enzyme from *Candida macedoniensis* Catalyzes the Stereospecific Reduction of the C=C Bond of Ketoisophorone," *Biosci. Biotechnol. Biochem.*, 66(12), pp. 2651-2657 (2002).
Miranda, M. et al., "Nucleotide Sequence and Chromosomal Localization of the Gene Encoding the Old Yellow Enzyme from *Kluyveromyces lactis*," *Yeast*, vol. 11, pp. 459-465 (1995).
Stott, K. et al., "Old Yellow Enzyme: The Discovery of Multiple Isozymes and a Family of Related Proteins," *J. Biol. Chem.*, vol. 268, No. 9, pp. 6097-6106 (1993).
Wada et al., "Production Of A Doubly Chiral Compound, (4R,6R)-4-Hydroxy-2,2,6-Trimethylcyclohexanone, By Two-Step Enzymatic Asymmetric Reduction," Applied and Environmental Microbiology, vol. 69, No. 2, pp. 933-937 (2003).
Kawai et al., "Asymmetric Reduction of alpha, beta-Unsaturated Ketones With A Carbon-Carbon Double," Tetrahedon Letters, vol. 39, No. 29, pp. 5225-5228 (1998).

* cited by examiner

*Primary Examiner*—Nashaat T Nashed
*Assistant Examiner*—Younus Meah
(74) *Attorney, Agent, or Firm*—Bryan Cave LLP

(57) ABSTRACT

Disclosed is an isolated DNA comprising a nucleotide sequence coding for an enzyme having enone reductase activity wherein the enzyme is characterized by the following physico-chemical properties: (a) molecular mass: 61,300±5,000 Da (estimated using gel filtration, consisting of one subunit); (b) co-factor: NADPH and NADH; (c) substrate specificity: active on $\alpha,\beta$-unsaturated ketons; (d) optimum temperature: 55-60° C. at pH 7.4; and (e) optimum pH: pH 4.5-8.5.

8 Claims, No Drawings

SEQUENCE LISTING

```
<160> NUMBER OF SEQ ID NOS: 32

<210> SEQ ID NO 1
<211> LENGTH: 1212
<212> TYPE: DNA
<213> ORGANISM: Candida kefyr
<220> FEATURE:
<221> NAME/KEY: CDS
<222> LOCATION: (1)..(1212)

<400> SEQUENCE: 1 atg tcg tac atg aac ttt gac cct aag cca ttg gga gac acc aat atc      48
Met Ser Tyr Met Asn Phe Asp Pro Lys Pro Leu Gly Asp Thr Asn Ile
1               5                   10                  15 ttc aag cca atc aag atc ggt aac aat gag cta aaa cac aga gta gtc      96
Phe Lys Pro Ile Lys Ile Gly Asn Asn Glu Leu Lys His Arg Val Val
            20                  25                  30 atg cca gca ttg act aga atg aga gcc att gca cca gga aac atc cca     144
Met Pro Ala Leu Thr Arg Met Arg Ala Ile Ala Pro Gly Asn Ile Pro
        35                  40                  45 aac act gaa tgg gcc gag gaa tac tac aga caa cgt tct caa tac cct     192
Asn Thr Glu Trp Ala Glu Glu Tyr Tyr Arg Gln Arg Ser Gln Tyr Pro
    50                  55                  60 ggt acc ctt att atc acg gaa ggt act ttc cct tct gcg caa tca ggt     240
Gly Thr Leu Ile Ile Thr Glu Gly Thr Phe Pro Ser Ala Gln Ser Gly
65                  70                  75                  80 ggt tac cca aat gtg cca ggt atc tgg tcc aaa gag caa ttg gct gaa     288
Gly Tyr Pro Asn Val Pro Gly Ile Trp Ser Lys Glu Gln Leu Ala Glu
                85                  90                  95 tgg aaa aag atc ttc aat gca atc cat gag aac aaa tcg ttc gtg tgg     336
Trp Lys Lys Ile Phe Asn Ala Ile His Glu Asn Lys Ser Phe Val Trp
            100                 105                 110 gtg caa ttg tgg gtt cta ggt aga caa gca tgg cca gaa gtg ttg aag     384
Val Gln Leu Trp Val Leu Gly Arg Gln Ala Trp Pro Glu Val Leu Lys
        115                 120                 125 aag gaa ggt ttg cgt tac gat agt gct acc gat gac ttg tac atg ggt     432
Lys Glu Gly Leu Arg Tyr Asp Ser Ala Thr Asp Asp Leu Tyr Met Gly
    130                 135                 140 gaa gaa gaa aaa gag cgt gcc tta aag gct aac aac cca cag cac ggt     480
Glu Glu Glu Lys Glu Arg Ala Leu Lys Ala Asn Asn Pro Gln His Gly
```

```
                145                 150                 155                 160
atc acc aag gaa gaa atc aag cag tac atc aag gag tac gtg gat gct        528
Ile Thr Lys Glu Glu Ile Lys Gln Tyr Ile Lys Glu Tyr Val Asp Ala
                165                 170                 175 gcc aag aaa gcc atc gat gca ggt gca gac ggt gtg caa atc cat tct        576
Ala Lys Lys Ala Ile Asp Ala Gly Ala Asp Gly Val Gln Ile His Ser
            180                 185                 190 gcc aac ggt tac ttg ttg aac cag ttt ttg gac cct att tct aac aac        624
Ala Asn Gly Tyr Leu Leu Asn Gln Phe Leu Asp Pro Ile Ser Asn Asn
        195                 200                 205 aga acc gac gag tac ggt gga tcg atc gag aac cgt gcg aga ttc act        672
Arg Thr Asp Glu Tyr Gly Gly Ser Ile Glu Asn Arg Ala Arg Phe Thr
    210                 215                 220 ttg gaa gtg gtc gat gcc gtt gtc gat gca gtt ggt gcc gaa aga acc        720
Leu Glu Val Val Asp Ala Val Val Asp Ala Val Gly Ala Glu Arg Thr
225                 230                 235                 240 tcc atc aga ttc tct cca tac ggt act ttt ggt acc atg tcc ggt ggt        768
Ser Ile Arg Phe Ser Pro Tyr Gly Thr Phe Gly Thr Met Ser Gly Gly
                245                 250                 255 gag aac cct ggc atc gtt gct caa tat gca tac gtc att ggt gag ttg        816
Glu Asn Pro Gly Ile Val Ala Gln Tyr Ala Tyr Val Ile Gly Glu Leu
            260                 265                 270 gaa aag aga gct aga gct ggc aag aga ttg gcg ttc atc gat ttg gtc        864
Glu Lys Arg Ala Arg Ala Gly Lys Arg Leu Ala Phe Ile Asp Leu Val
        275                 280                 285 gag cct cgt gtg acc gac cca ttc cta cca gaa ttc gag aag tgg ttc        912
Glu Pro Arg Val Thr Asp Pro Phe Leu Pro Glu Phe Glu Lys Trp Phe
    290                 295                 300 aag gaa ggt acc aac gaa ttc atc tac tct atc tgg aag ggt cca gtt        960
Lys Glu Gly Thr Asn Glu Phe Ile Tyr Ser Ile Trp Lys Gly Pro Val
305                 310                 315                 320 ctc aga gtt ggt aac tat gct ttg gac cca gat caa gcc act ctc gac       1008
Leu Arg Val Gly Asn Tyr Ala Leu Asp Pro Asp Gln Ala Thr Leu Asp
                325                 330                 335 tct aag aag cct aac act ttg atc ggt tac ggt aga tcc ttc atc gcc       1056
Ser Lys Lys Pro Asn Thr Leu Ile Gly Tyr Gly Arg Ser Phe Ile Ala
            340                 345                 350 aac cca gac ttg gtg tac cgt ttg gaa aag ggt ttg cca ttg aac aag       1104
Asn Pro Asp Leu Val Tyr Arg Leu Glu Lys Gly Leu Pro Leu Asn Lys
        355                 360                 365 tat gat aga aac acc ttt tac aca ttc act aag gaa ggt tac acc gat       1152
Tyr Asp Arg Asn Thr Phe Tyr Thr Phe Thr Lys Glu Gly Tyr Thr Asp
    370                 375                 380 tac cca agc tac gaa gaa tcc gtc gca aag ggt tac aag aaa gag gaa       1200
Tyr Pro Ser Tyr Glu Glu Ser Val Ala Lys Gly Tyr Lys Lys Glu Glu
385                 390                 395                 400 aag aag tac taa                                                        1212
Lys Lys Tyr <210> SEQ ID NO 2
<211> LENGTH: 403
<212> TYPE: PRT
<213> ORGANISM: Candida kefyr

<400> SEQUENCE: 2

Met Ser Tyr Met Asn Phe Asp Pro Lys Pro Leu Gly Asp Thr Asn Ile
1               5                   10                  15

Phe Lys Pro Ile Lys Ile Gly Asn Asn Glu Leu Lys His Arg Val Val
            20                  25                  30
```

```
Met Pro Ala Leu Thr Arg Met Arg Ala Ile Ala Pro Gly Asn Ile Pro
            35                  40                  45

Asn Thr Glu Trp Ala Glu Glu Tyr Tyr Arg Gln Arg Ser Gln Tyr Pro
 50                  55                  60

Gly Thr Leu Ile Ile Thr Glu Gly Thr Phe Pro Ser Ala Gln Ser Gly
 65                  70                  75                  80

Gly Tyr Pro Asn Val Pro Gly Ile Trp Ser Lys Glu Gln Leu Ala Glu
                 85                  90                  95

Trp Lys Lys Ile Phe Asn Ala Ile His Glu Asn Lys Ser Phe Val Trp
                100                 105                 110

Val Gln Leu Trp Val Leu Gly Arg Gln Ala Trp Pro Glu Val Leu Lys
            115                 120                 125

Lys Glu Gly Leu Arg Tyr Asp Ser Ala Thr Asp Leu Tyr Met Gly
130                 135                 140

Glu Glu Glu Lys Glu Arg Ala Leu Lys Ala Asn Asn Pro Gln His Gly
145                 150                 155                 160

Ile Thr Lys Glu Glu Ile Lys Gln Tyr Ile Lys Glu Tyr Val Asp Ala
                165                 170                 175

Ala Lys Lys Ala Ile Asp Ala Gly Ala Asp Gly Val Gln Ile His Ser
            180                 185                 190

Ala Asn Gly Tyr Leu Leu Asn Gln Phe Leu Asp Pro Ile Ser Asn Asn
            195                 200                 205

Arg Thr Asp Glu Tyr Gly Gly Ser Ile Glu Asn Arg Ala Arg Phe Thr
            210                 215                 220

Leu Glu Val Val Asp Ala Val Val Asp Ala Val Gly Ala Glu Arg Thr
225                 230                 235                 240

Ser Ile Arg Phe Ser Pro Tyr Gly Thr Phe Gly Thr Met Ser Gly Gly
                245                 250                 255

Glu Asn Pro Gly Ile Val Ala Gln Tyr Ala Tyr Val Ile Gly Glu Leu
            260                 265                 270

Glu Lys Arg Ala Arg Ala Gly Lys Arg Leu Ala Phe Ile Asp Leu Val
            275                 280                 285

Glu Pro Arg Val Thr Asp Pro Phe Leu Pro Glu Phe Glu Lys Trp Phe
            290                 295                 300

Lys Glu Gly Thr Asn Glu Phe Ile Tyr Ser Ile Trp Lys Gly Pro Val
305                 310                 315                 320

Leu Arg Val Gly Asn Tyr Ala Leu Asp Pro Asp Gln Ala Thr Leu Asp
                325                 330                 335

Ser Lys Lys Pro Asn Thr Leu Ile Gly Tyr Gly Arg Ser Phe Ile Ala
            340                 345                 350

Asn Pro Asp Leu Val Tyr Arg Leu Glu Lys Gly Leu Pro Leu Asn Lys
            355                 360                 365

Tyr Asp Arg Asn Thr Phe Tyr Thr Phe Thr Lys Glu Gly Tyr Thr Asp
            370                 375                 380

Tyr Pro Ser Tyr Glu Glu Ser Val Ala Lys Gly Tyr Lys Lys Glu Glu
385                 390                 395                 400

Lys Lys Tyr

<210> SEQ ID NO 3
<211> LENGTH: 12
<212> TYPE: PRT
<213> ORGANISM: Candida kefyr

<400> SEQUENCE: 3
```

```
Pro Leu Gly Asp Thr Asn Ile Phe Lys Pro Ile Lys
1               5                   10

<210> SEQ ID NO 4
<211> LENGTH: 50
<212> TYPE: PRT
<213> ORGANISM: Candida kefyr

<400> SEQUENCE: 4

His Arg Val Val Met Pro Ala Leu Thr Arg Met Arg Ala Ile Ala Pro
1               5                   10                  15

Gly Asn Ile Pro Asn Thr Glu Trp Ala Glu Glu Tyr Tyr Arg Gln Arg
            20                  25                  30

Ser Gln Tyr Pro Gly Thr Leu Ile Ile Thr Glu Gly Thr Phe Pro Ser
        35                  40                  45

Val Gln
    50

<210> SEQ ID NO 5
<211> LENGTH: 8
<212> TYPE: PRT
<213> ORGANISM: Candida kefyr

<400> SEQUENCE: 5

Glu Gln Leu Ala Glu Trp Lys Lys
1               5

<210> SEQ ID NO 6
<211> LENGTH: 9
<212> TYPE: PRT
<213> ORGANISM: Candida kefyr

<400> SEQUENCE: 6

Ile Phe Asn Ala Ile His Glu Asn Lys
1               5

<210> SEQ ID NO 7
<211> LENGTH: 18
<212> TYPE: PRT
<213> ORGANISM: Candida kefyr
<220> FEATURE:
<221> NAME/KEY: MISC_FEATURE
<222> LOCATION: (15)..(15)
<220> FEATURE:
<221> NAME/KEY: MISC_FEATURE
<222> LOCATION: (15)..(15)
<223> OTHER INFORMATION: Xaa is unknown

<400> SEQUENCE: 7

Ser Phe Val Trp Val Gln Leu Trp Val Leu Gly Arg Gln Ala Xaa Pro
1               5                   10                  15

Glu Val

<210> SEQ ID NO 8
<211> LENGTH: 19
<212> TYPE: PRT
<213> ORGANISM: Candida kefyr

<400> SEQUENCE: 8

Glu Gly Leu Arg Tyr Asp Ser Ala Phe Asp Leu Tyr Met Gly Glu
1               5                   10                  15

Glu Glu Lys
```

```
<210> SEQ ID NO 9
<211> LENGTH: 10
<212> TYPE: PRT
<213> ORGANISM: Candida kefyr

<400> SEQUENCE: 9

Ala Asn Asn Pro Gln His Gly Ile Thr Lys
1               5                   10

<210> SEQ ID NO 10
<211> LENGTH: 7
<212> TYPE: PRT
<213> ORGANISM: Candida kefyr

<400> SEQUENCE: 10

Glu Tyr Val Asp Ala Ala Lys
1               5

<210> SEQ ID NO 11
<211> LENGTH: 50
<212> TYPE: PRT
<213> ORGANISM: Candida kefyr
<220> FEATURE:
<221> NAME/KEY: MISC_FEATURE
<222> LOCATION: (43)..(43)
<223> OTHER INFORMATION: Xaa is unknown
<220> FEATURE:
<221> NAME/KEY: MISC_FEATURE
<222> LOCATION: (45)..(45)
<223> OTHER INFORMATION: Xaa is unknown
<220> FEATURE:
<221> NAME/KEY: MISC_FEATURE
<222> LOCATION: (47)..(48)
<223> OTHER INFORMATION: Xaa is unknown

<400> SEQUENCE: 11

Ala Ile Asp Ala Gly Ala Asp Gly Val Gln Ile His Ser Ala Asn Gly
1               5                   10                  15

Tyr Leu Leu Asn Gln Phe Leu Asp Pro Ile Ser Asn Asn Arg Thr Asp
            20                  25                  30

Glu Tyr Gly Gly Ser Ile Ile Asn Arg Ala Xaa Phe Xaa Leu Xaa Xaa
        35                  40                  45

Val Asp
    50

<210> SEQ ID NO 12
<211> LENGTH: 22
<212> TYPE: PRT
<213> ORGANISM: Candida kefyr

<400> SEQUENCE: 12

Arg Leu Ala Phe Ile Asp Leu Val Glu Pro Arg Val Thr Asp Pro Phe
1               5                   10                  15

Leu Pro Glu Phe Glu Lys
            20

<210> SEQ ID NO 13
<211> LENGTH: 12
<212> TYPE: PRT
<213> ORGANISM: Candida kefyr

<400> SEQUENCE: 13

Glu Gly Thr Asn Glu Phe Ile Tyr Ser Ile Trp Lys
1               5                   10
```

```
<210> SEQ ID NO 14
<211> LENGTH: 21
<212> TYPE: PRT
<213> ORGANISM: Candida kefyr

<400> SEQUENCE: 14

Gly Pro Val Leu Arg Val Gly Asn Tyr Ala Leu Asp Pro Asp Gln Ala
1               5                   10                  15

Thr Leu Asp Ser Lys
            20

<210> SEQ ID NO 15
<211> LENGTH: 24
<212> TYPE: PRT
<213> ORGANISM: Candida kefyr

<400> SEQUENCE: 15

Leu Pro Asn Thr Leu Ile Gly Tyr Gly Arg Ser Phe Ile Ala Asn Pro
1               5                   10                  15

Asp Leu Val Tyr Arg Leu Glu Lys
            20

<210> SEQ ID NO 16
<211> LENGTH: 6
<212> TYPE: PRT
<213> ORGANISM: Candida kefyr

<400> SEQUENCE: 16

Gly Leu Pro Leu Asn Lys
1               5

<210> SEQ ID NO 17
<211> LENGTH: 11
<212> TYPE: PRT
<213> ORGANISM: Candida kefyr

<400> SEQUENCE: 17

Tyr Asp Arg Asn Thr Phe Tyr Thr Phe Thr Lys
1               5                   10

<210> SEQ ID NO 18
<211> LENGTH: 15
<212> TYPE: PRT
<213> ORGANISM: Candida kefyr

<400> SEQUENCE: 18

Glu Gly Tyr Thr Asp Tyr Pro Ser Tyr Glu Glu Ser Val Ala Lys
1               5                   10                  15

<210> SEQ ID NO 19
<211> LENGTH: 9
<212> TYPE: PRT
<213> ORGANISM: Candida kefyr

<400> SEQUENCE: 19

Gly Asp Thr Asn Ile Phe Lys Pro Ile
1               5

<210> SEQ ID NO 20
<211> LENGTH: 9
<212> TYPE: PRT
<213> ORGANISM: Artificial Sequence
<220> FEATURE:
<223> OTHER INFORMATION: reverse sequence of a partial amino acid
      sequence of enone reductase
```

```
<400> SEQUENCE: 20

Gly Glu Lys Thr Phe Thr Tyr Phe Thr
1               5

<210> SEQ ID NO 21
<211> LENGTH: 1058
<212> TYPE: DNA
<213> ORGANISM: Candida kefyr
<220> FEATURE:
<221> NAME/KEY: CDS
<222> LOCATION: (1)..(1056)

<400> SEQUENCE: 21 cac aga gta gtc atg cca gca ttg act aga atg aga gcc att gca cca       48
His Arg Val Val Met Pro Ala Leu Thr Arg Met Arg Ala Ile Ala Pro
1               5                   10                  15 gga aac atc cca aac act gaa tgg gcc gag gaa tac tac aga caa cgt       96
Gly Asn Ile Pro Asn Thr Glu Trp Ala Glu Glu Tyr Tyr Arg Gln Arg
                20                  25                  30 tct caa tac cct ggt acc ctt att atc acg gaa ggt act ttc cct tct      144
Ser Gln Tyr Pro Gly Thr Leu Ile Ile Thr Glu Gly Thr Phe Pro Ser
            35                  40                  45 gcg caa tca ggt ggt tac cca aat gtg cca ggt atc tgg tcc aaa gag      192
Ala Gln Ser Gly Gly Tyr Pro Asn Val Pro Gly Ile Trp Ser Lys Glu
        50                  55                  60 caa ttg gct gaa tgg aaa aag atc ttc aat gca atc cat gag aac aaa      240
Gln Leu Ala Glu Trp Lys Lys Ile Phe Asn Ala Ile His Glu Asn Lys
65                  70                  75                  80 tcg ttc gtg tgg gtg caa ttg tgg gtt cta ggt aga caa gca tgg cca      288
Ser Phe Val Trp Val Gln Leu Trp Val Leu Gly Arg Gln Ala Trp Pro
                85                  90                  95 gaa gtg ttg aag aag gaa ggt ttg cgt tac gat agt gct acc gat gac      336
Glu Val Leu Lys Lys Glu Gly Leu Arg Tyr Asp Ser Ala Thr Asp Asp
                100                 105                 110 ttg tac atg ggt gaa gaa gaa aaa gag cgt gcc tta aag gct aac aac      384
Leu Tyr Met Gly Glu Glu Glu Lys Glu Arg Ala Leu Lys Ala Asn Asn
            115                 120                 125 cca cag cac ggt atc acc aag gaa gaa atc aag cag tac atc aag gag      432
Pro Gln His Gly Ile Thr Lys Glu Glu Ile Lys Gln Tyr Ile Lys Glu
        130                 135                 140 tac gtg gat gct gcc aag aaa gcc atc gat gca ggt gca gac ggt gtg      480
Tyr Val Asp Ala Ala Lys Lys Ala Ile Asp Ala Gly Ala Asp Gly Val
145                 150                 155                 160 caa atc cat tct gcc aac ggt tac ttg ttg aac cag ttt ttg gac cct      528
Gln Ile His Ser Ala Asn Gly Tyr Leu Leu Asn Gln Phe Leu Asp Pro
                165                 170                 175 att tct aac aac aga acc gac gag tac ggt gga tcg atc gag aac cgt      576
Ile Ser Asn Asn Arg Thr Asp Glu Tyr Gly Gly Ser Ile Glu Asn Arg
                180                 185                 190 gcg aga ttc act ttg gaa gtg gtt gat gcc gtt gta gat gca gtt ggt      624
Ala Arg Phe Thr Leu Glu Val Val Asp Ala Val Val Asp Ala Val Gly
            195                 200                 205 gcc gaa aga acc tcc atc aga ttc tct cct tac ggt act ttt ggt acc      672
Ala Glu Arg Thr Ser Ile Arg Phe Ser Pro Tyr Gly Thr Phe Gly Thr
        210                 215                 220 atg tcc ggt ggt gag aac cct ggc atc gtt gcc caa tat gca tac gtc      720
Met Ser Gly Gly Glu Asn Pro Gly Ile Val Ala Gln Tyr Ala Tyr Val
225                 230                 235                 240 att ggt gag ttg gaa aag aga gct aga gct ggc aag aga ttg gcc ttc      768
Ile Gly Glu Leu Glu Lys Arg Ala Arg Ala Gly Lys Arg Leu Ala Phe
```

```
                    245                 250                 255
atc gat ttg gtc gag cct cgt gtg acc gac cca ttc cta cca gaa ttc       816
Ile Asp Leu Val Glu Pro Arg Val Thr Asp Pro Phe Leu Pro Glu Phe
            260                 265                 270 gag aag tgg ttc aag gaa ggt acc aac gaa ttc atc tac tct atc tgg       864
Glu Lys Trp Phe Lys Glu Gly Thr Asn Glu Phe Ile Tyr Ser Ile Trp
        275                 280                 285 aag ggt cca gtt ctc aga gtt ggt aac tat gct ttg gac cca gat caa       912
Lys Gly Pro Val Leu Arg Val Gly Asn Tyr Ala Leu Asp Pro Asp Gln
    290                 295                 300 gct act atc gac tct aag aag cct aac acc ttg atc ggt tac ggt aga       960
Ala Thr Ile Asp Ser Lys Lys Pro Asn Thr Leu Ile Gly Tyr Gly Arg
305                 310                 315                 320 tcc ttt att gcc aac cca gac ttg gtg tac cgt ttg gaa aag ggt ttg      1008
Ser Phe Ile Ala Asn Pro Asp Leu Val Tyr Arg Leu Glu Lys Gly Leu
                325                 330                 335 cca ttg aac aag tat gat aga aac acc ttc tac acc ttc acc aaa gag      1056
Pro Leu Asn Lys Tyr Asp Arg Asn Thr Phe Tyr Thr Phe Thr Lys Glu
            340                 345                 350 gg                                                                   1058

<210> SEQ ID NO 22
<211> LENGTH: 352
<212> TYPE: PRT
<213> ORGANISM: Candida kefyr

<400> SEQUENCE: 22

His Arg Val Val Met Pro Ala Leu Thr Arg Met Arg Ala Ile Ala Pro
1               5                   10                  15

Gly Asn Ile Pro Asn Thr Glu Trp Ala Glu Glu Tyr Tyr Arg Gln Arg
            20                  25                  30

Ser Gln Tyr Pro Gly Thr Leu Ile Ile Thr Glu Gly Thr Phe Pro Ser
        35                  40                  45

Ala Gln Ser Gly Gly Tyr Pro Asn Val Pro Gly Ile Trp Ser Lys Glu
    50                  55                  60

Gln Leu Ala Glu Trp Lys Lys Ile Phe Asn Ala Ile His Glu Asn Lys
65                  70                  75                  80

Ser Phe Val Trp Val Gln Leu Trp Val Leu Gly Arg Gln Ala Trp Pro
                85                  90                  95

Glu Val Leu Lys Lys Glu Gly Leu Arg Tyr Asp Ser Ala Thr Asp Asp
            100                 105                 110

Leu Tyr Met Gly Glu Glu Glu Lys Glu Arg Ala Leu Lys Ala Asn Asn
        115                 120                 125

Pro Gln His Gly Ile Thr Lys Glu Glu Ile Lys Gln Tyr Ile Lys Glu
    130                 135                 140

Tyr Val Asp Ala Ala Lys Lys Ala Ile Asp Ala Gly Ala Asp Gly Val
145                 150                 155                 160

Gln Ile His Ser Ala Asn Gly Tyr Leu Leu Asn Gln Phe Leu Asp Pro
                165                 170                 175

Ile Ser Asn Asn Arg Thr Asp Glu Tyr Gly Gly Ser Ile Glu Asn Arg
            180                 185                 190

Ala Arg Phe Thr Leu Glu Val Val Asp Ala Val Val Asp Ala Val Gly
        195                 200                 205

Ala Glu Arg Thr Ser Ile Arg Phe Ser Pro Tyr Gly Thr Phe Gly Thr
    210                 215                 220

Met Ser Gly Gly Glu Asn Pro Gly Ile Val Ala Gln Tyr Ala Tyr Val
```

```
                225                 230                 235                 240
Ile Gly Glu Leu Glu Lys Arg Ala Arg Ala Gly Lys Arg Leu Ala Phe
                245                 250                 255

Ile Asp Leu Val Glu Pro Arg Val Thr Asp Pro Phe Leu Pro Glu Phe
            260                 265                 270

Glu Lys Trp Phe Lys Glu Gly Thr Asn Glu Phe Ile Tyr Ser Ile Trp
        275                 280                 285

Lys Gly Pro Val Leu Arg Val Gly Asn Tyr Ala Leu Asp Pro Asp Gln
        290                 295                 300

Ala Thr Ile Asp Ser Lys Lys Pro Asn Thr Leu Ile Gly Tyr Gly Arg
305                 310                 315                 320

Ser Phe Ile Ala Asn Pro Asp Leu Val Tyr Arg Leu Glu Lys Gly Leu
                325                 330                 335

Pro Leu Asn Lys Tyr Asp Arg Asn Thr Phe Tyr Thr Phe Thr Lys Glu
            340                 345                 350

<210> SEQ ID NO 23
<211> LENGTH: 25
<212> TYPE: DNA
<213> ORGANISM: Artificial Sequence
<220> FEATURE:
<223> OTHER INFORMATION: IA1 (antisense primer for upstream region)

<400> SEQUENCE: 23
attcctcggc ccattcagtg ttggg                                          25

<210> SEQ ID NO 24
<211> LENGTH: 26
<212> TYPE: DNA
<213> ORGANISM: Artificial Sequence
<220> FEATURE:
<223> OTHER INFORMATION: IS1 (sense primer for downstream region)

<400> SEQUENCE: 24
ggtgtaccgt ttggaaaagg gtttgc                                         26

<210> SEQ ID NO 25
<211> LENGTH: 1796
<212> TYPE: DNA
<213> ORGANISM: Candida kefyr

<400> SEQUENCE: 25
tatatatata tatatgtata tatttaggtt aatactgagt atttgactta gaataaagaa      60
ggctaatatt ggtagtagta gtggtagcag ttagagcatc tgcagcaccg agacctaact     120
aattaattat atcaacaaac tgtcgagatg tcgtacatga actttgaccc taagccattg     180
ggagacacca atatcttcaa gccaatcaag atcggtaaca atgagctaaa acacagagta     240
gtcatgccag cattgactag aatgagagcc attgcaccag aaacatccc aaacactgaa      300 tgggccgagg aatactacag acaacgttct caatacctg gtacccttat tatcacggaa      360
ggtactttcc cttctgcgca atcaggtggt tacccaaatg tgccaggtat ctggtccaaa     420
gagcaattgg ctgaatggaa aaagatcttc aatgcaatcc atgagaacaa atcgttcgtg     480
tgggtgcaat gtgggttct aggtagacaa gcatggccag aagtgttgaa gaaggaaggt      540
ttgcgttacg atagtgctac cgatgacttg tacatgggtg aagaagaaaa agagcgtgcc     600
ttaaaggcta acaacccaca gcacggtatc accaaggaag aaatcaagca gtacatcaag     660
gagtacgtgg atgctgccaa gaaagccatc gatgcaggtg cagacggtgt gcaaatccat     720
```

```
tctgccaacg gttacttgtt gaaccagttt ttggaccota tttctaacaa cagaaccgac      780
gagtacggtg gatcgatcga gaaccgtgcg agattcactt tggaagtggt tgatgccgtt      840
gtagatgcag ttggtgccga aagaacctcc atcagattct ctccttacgg tacttttggt      900
accatgtccg gtggtgagaa ccctggcatc gttgcccaat atgcatacgt cattggtgag      960
ttggaaaaga gagctagagc tgcaagagaa ttggccttca tcgatttggt cgagcctcgt      1020
gtgaccgacc cattcctacc agaattcgag aagtggttca aggaaggtac caacgaattc      1080
atctactcta tctggaaggg tccagttctc agagttggta actatgcttt ggacccagat      1140
caagctacta tcgactctaa gaagcctaac accttgatcg gttacggtag atccttattt      1200
gccaacccag acttggtgta ccgtttggaa aagggtttgc cattgaacaa gtatgataga      1260
aacaccttct acaccttcac caaagaaggt tacaccgatt acccaagcta cgaggaatcc      1320
gtcgcaaagg gttacaagaa agaggaaaag aagtactaag cttgaactga taactagcca      1380
ggaccagaat ctgtcatcct ctctactttc taattaattt ttatgtatga tggatgactt      1440
taatattata ttattatata atacatatgc ctaaactaac tactacactt gggaaattgg      1500
tggcagatga ggggcctttg accttcaatg tttgtatgta agtaatgatt caaaagattc      1560
tcctctatag ttggttagtt actactaaaa gaaaccttca atataaaaca atgatcgaga      1620
atacattatt aaattaacct atgaatttat aaaataaaag agataaaata aaattaaaaa      1680
ctaccattaa gtctttgtgc gaaatgagta accttatatt aataaaagat gtgaagtgtg      1740
gtgtacgtgt gcgtgtacgt gcgtgtgcaa aatttgtgtg tgtttaagtg taaaat          1796

<210> SEQ ID NO 26
<211> LENGTH: 20
<212> TYPE: DNA
<213> ORGANISM: Artificial Sequence
<220> FEATURE:
<223> OTHER INFORMATION: Sense Primer

<400> SEQUENCE: 26
gagcatctgc agcaccgaga                                                  20

<210> SEQ ID NO 27
<211> LENGTH: 20
<212> TYPE: DNA
<213> ORGANISM: Artificial Sequence
<220> FEATURE:
<223> OTHER INFORMATION: Antisense Primer

<400> SEQUENCE: 27
gagaggatga cagattctgg                                                  20

<210> SEQ ID NO 28
<211> LENGTH: 1310
<212> TYPE: DNA
<213> ORGANISM: Candida kefyr

<400> SEQUENCE: 28
gagcatctgc agcaccgaga cctaactaat taattatatc aacaaactgt cgagatgtcg      60
tacatgaact ttgaccctaa gccattggga gacaccaata tcttcaagcc aatcaagatc      120
ggtaacaatg agctaaaaca cagagtagtc atgccagcat tgactagaat gagagccatt      180
gcaccaggaa acatcccaaa cactgaatgg gccgaggaat actacagaca acgttctcaa      240
taccctggta cccttattat cacggaaggt actttcccctt ctgcgcaatc aggtggttac      300
ccaaatgtgc caggtatctg gtccaaagag caattggctg aatggaaaaa gatcttcaat      360
```

-continued

```
gcaatccatg agaacaaatc gttcgtgtgg gtgcaattgt gggttctagg tagacaagca    420
tggccagaag tgttgaagaa ggaaggtttg cgttacgata gtgctaccga tgacttgtac    480
atgggtgaag aagaaaaaga gcgtgcctta aaggctaaca acccacagca cggtatcacc    540
aaggaagaaa tcaagcagta catcaaggag tacgtggatg ctgccaagaa agccatcgat    600
gcaggtgcag acggtgtgca aatccattct gccaacggtt acttgttgaa ccagttttg    660 gaccctattt ctaacaacag aaccgacgag tacggtggat cgatcgagaa ccgtgcgaga    720
ttcactttgg aagtggtcga tgccgttgtc gatgcagttg gtgccgaaag aacctccatc    780
agattctctc catacggtac ttttggtacc atgtccggtg gtgagaaccc tggcatcgtt    840
gctcaatatg catacgtcat tggtgagttg gaaaagagag ctagagctgg caagagattg    900
gcgttcatcg atttggtcga gcctcgtgtg accgacccat tcctaccaga attcgagaag    960
tggttcaagg aagtaccaa cgaattcatc tactctatct ggaagggtcc agttctcaga   1020
gttggtaact atgctttgga cccagatcaa gccactctcg actctaagaa gcctaacact   1080
ttgatcggtt acggtagatc cttcatcgcc aacccagact ggtgtaccg tttggaaaag   1140 ggtttgccat tgaacaagta tgatagaaac acctttaca cattcactaa ggaaggttac   1200
accgattacc caagctacga agaatccgtc gcaagggtt acaagaaaga ggaaagaag   1260 tactaagctt gaactgataa ctagccagga ccagaatctg tcatcctctc              1310
```

<210> SEQ ID NO 29
<211> LENGTH: 25
<212> TYPE: DNA
<213> ORGANISM: Artificial Sequence
<220> FEATURE:
<223> OTHER INFORMATION: Primer ExS

<400> SEQUENCE: 29
caccatgtcg tacatgaact ttgac         25

<210> SEQ ID NO 30
<211> LENGTH: 29
<212> TYPE: DNA
<213> ORGANISM: Artificial Sequence
<220> FEATURE:
<223> OTHER INFORMATION: Primer ExA

<400> SEQUENCE: 30
ttagtacttc ttttcctctt tcttgtaac      29

<210> SEQ ID NO 31
<211> LENGTH: 26
<212> TYPE: DNA
<213> ORGANISM: Artificial Sequence
<220> FEATURE:
<223> OTHER INFORMATION: degenerate Primer encoding SEQ ID NO:19
<220> FEATURE:
<221> NAME/KEY: modified_base
<222> LOCATION: (3)..(3)
<223> OTHER INFORMATION: I
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (24)..(24)
<223> OTHER INFORMATION: n is a or c or g or t

<400> SEQUENCE: 31

```
ggagayacaa ayathttyaa rccnat                                    26

<210> SEQ ID NO 32
<211> LENGTH: 26
<212> TYPE: DNA
<213> ORGANISM: Artificial Sequence
<220> FEATURE:
<223> OTHER INFORMATION: degenerate Primer encoding SEQ ID NO:20
<220> FEATURE:
<221> NAME/KEY: misc_feature
<222> LOCATION: (9)..(9)
<223> OTHER INFORMATION: n is a or c or g or t
<220> FEATURE:
<221> NAME/KEY: modified_base
<222> LOCATION: (15)..(15)
<223> OTHER INFORMATION: I
<220> FEATURE:
<221> NAME/KEY: modified_base
<222> LOCATION: (24)..(24)
<223> OTHER INFORMATION: I

<400> SEQUENCE: 32
ccytcyttng traaagtrta raaagt                                    26
```

US 7,592,166 B2

ENONE REDUCTASE GENE AND MICROBIAL PRODUCTION OF LEVODIONE

This application is the National Stage of International Application No. PCT/EP2003/010473, filed Sep. 19, 2003.

The present invention relates to a DNA encoding an enone reductase, an expression vector comprising the DNA, a microorganism into which the DNA has been introduced, and a method for producing (6R)-2,2,6-trimethyl-1,4-cyclohexanedione (hereinafter referred to as levodione) from 2,6,6-trimethly-2-cyclohexene-1,4-dione (hereinafter referred to as ketoisophorone) using the microorganism.

Levodione is a useful intermediate in the synthesis of optically active carotenoids such as zeaxanthin. A microbiological process of producing levodione from ketoisophorone is known (U.S. Pat. No. 4,156,100). Enone reductase that acts on ketoisophorone to produce levodione, which was isolated from *Candida kefyr* was described in (European Patent Application No. 02003967.3 filed on Feb. 22, 2002). This enzyme is characterized by the following physico-chemical properties:
(a) molecular mass: 61,300±5,000 Da
 (Estimated using gel filtration. Consisting of one subunit.)
(b) Co-factor: NADPH and NADH
(c) Substrate specificity: active on α,β-unsaturated ketons
(d) Optimum temperature: 55-60° C. at pH 7.4
(e) Optimum pH: pH 4.5-8.5

As used herein, the term "enone reductase" encompasses proteins catalyzing the enzymatic reduction of carbonyl activated double bonds according to the Enzyme Nomenclature provided by the Nomenclature Committee of the International Union of Biochemistry and Molecular Biology (NC-IUBMB). It also relates to proteins having the above mentioned activities of an enone reductase, which proteins preferably catalyse the conversion of ketoisophorone into levodione. The gene for an enone reductase involved in the biosynthesis of levodione would be very useful for improvement of levodione productivity by a microorganism.

The present invention provides to an isolated DNA sequence encoding enone reductase.

The isolated DNA sequence may be more specifically characterized in that (a) it codes for the enzyme having the amino acid sequence described in SEQ ID NO:2, or (b) it codes for a variant of the enzyme selected from (i) an allelic variant, and (ii) an enzyme having one or more amino acid addition, insertion, deletion and/or substitution and having the stated enzyme activity.

More particularly, the present invention provides an isolated DNA sequence derived from a gene of *Candida kefyr* (*Candida macedoniensis*) IFO 0960 and is selected from (i) the DNA sequence represented in SEQ ID NO:1, (ii) an isocoding or an allelic variant of the DNA sequence represented in SEQ ID NO:1, (iii) a derivative of the DNA sequence represented in SEQ ID NO:1, with addition, insertion, deletion and/or substitution of one or more nucleotide(s) and coding for a polypeptide having the enzyme activity, (iv) the DNA sequence which hybridizes to the complement of the nucleotide sequence of (i) or (ii) under stringent hybridizing conditions and coding for a polypeptide having the enzyme activity, and (v) the DNA sequence which is at least 80% identical to the nucleotide sequence of (i) and coding for a polypeptide having the enzyme activity.

The strain *Candida kefyr* (*Candida macedoniensis*) IFO 0960 is publicly available from the Institute for Fermentation Osaka (IFO), 17-85 Juso-honmachi 2-chome, Yodogawa-ku, Osaka, 532-8686, Japan.

Instructions for identifying DNA sequences by means of hybridization are well-known to a person skilled in the art. The hybridization may take place under stringent conditions wherein only hybrids in which the probe and target sequence, i.e. the polynucleotides treated with the probe and are at least 70% identical, are formed. It is known that the stringency of the hybridization, including the washing steps, is influenced or determined by varying the buffer composition, the temperature and the salt concentration. The hybridization reaction is preferably carried out under a relatively low stringency compared with the washing steps.

A 5×SSC buffer at a temperature of approx. 50-68° C., for example, can be employed for the hybridization reaction. Probes can also hybridize here with polynucleotides that are less than 70% identical to the sequence of the probe. Such hybrids are less stable and are removed by washing under stringent conditions. This can be achieved, for example, by lowering the salt concentration to 2×SSC and subsequently 0.5×SSC at a temperature of approx. 50-68° C. being established. It is optionally possible to lower the salt concentration to 0.1×SSC. Polynucleotide fragment, for example, at least 70% or at least 80%, or at least 90% to 95% identical to the sequence of the probe employed can be isolated by increasing the hybridization temperature stepwise in steps of approx. 1-2° C.

"Stringent conditions" in the context of this invention mean hybridization in a buffer, for example, consisting of 5 ×SSC, 0.1% (w/v) N-lauroylsarcosine, 0.02%(w/v) SDS, 1% blocking reagent (Roche Diagnostics, Cat. No. 1096 176) at 50° C. overnight and two times of washing with 2×SSC, 0.1% (w/v) SDS for 5 min. at room temperature and following two times of washing with 0.1×SSC, 0.1% (w/v) SDS for 15 min. at 68° C. in the washing step of hybridization.

The DNA sequence may be cloned from a strain of *C. kefyr* (*C. macedoniensis*) IFO 0960, or another or related organism and thus, for example, may be an allelic or species variant of an enone reductase encoding region of the DNA sequence. Also included within the scope of the present invention is a derivative of the DNA sequence with addition, insertion, deletion and/or substitution of different nucleotides resulting in a polypeptide that encodes the same or a functionally equivalent levodione reductase. The encoded protein may also contain addition, deletion, insertion and/or substitution of amino acid residues, which produce a silent change and result in a functionally equivalent enone reductase.

The DNA of the present invention also means a genomic DNA that contains regulatory sequences such as a promoter and a terminator, which are involved in the expression of the gene of interest, and also a cDNA that contains only open reading frame flanked between the short fragments in its 5'- and 3'-untranslated region.

The enone reductase gene, the recombinant expression vector, and the recombinant organisms utilized in the present invention may be obtained by the following steps:

Isolating chromosomal DNA from a microorganism that can provide enone reductase of the present invention and constructing the gene library with the chromosomal DNA.

Cloning an enone reductase gene from the chromosomal DNA by colony- or plaque-hybridization, PCR cloning, Southern-blot hybridization and so on.

Determining nucleotide sequence of the enone reductase gene obtained as above by usual methods and constructing recombinant expression vectors which contain and express the enone reductase gene efficiently.

Constructing recombinant organisms carrying the enone reductase gene on recombinant expression vectors or on chromosomes by transformation, transduction, transconjugation or electroporation.

The techniques used to isolate or clone a DNA encoding enone reductase of the present invention are known in the art and include isolation from genomic DNA. The cloning of the DNA sequence of the present invention from such genomic DNA can be effected by using the degenerate polymerase chain reaction (hereinafter referred to as PCR).

On the basis of information on the partial amino acid sequence oligonucleotides as primers for PCR may be synthesized. The primers used for cloning of the enone reductase gene by PCR may be based on the amino acid sequence of the peptide fragments of the purified enone reductase from the genera including, but not to limited to, *Candida* and *Zygosaccharomyces*, and in the most preferred embodiment, from *C. kefyr* (*C. macedoniensis*) IFO 0960. A DNA fragment (a partial DNA sequence) of enone reductase is generated by PCR amplification with the primers and the template of, e.g., *C. kefyr* chromosomal DNA. The amplified DNA fragment can be used as the probe to clone a genomic fragment coding for the whole enone reductase. An entire gene containing its coding region as well as its regulation region such as a promoter or terminator can be cloned from a chromosome, for example, by inverse PCR method using primers based on part of sequence of the obtained DNA fragment after it was sequenced, or screening of genomic library which is constructed in phage vector or plasmid vector in an appropriate host, by using a partial DNA fragment obtained by PCR as described above as a probe after it was labeled.

Generally, *E. coli* as a host strain and *E. coli* vector, a phage vector such as λ phage vector, a plasmid vector, or a yeast vector is often used in the construction of library and a following genetic manipulation such as sequencing, restriction digestion, ligation and so on. After the isolation of all necessary parts of the entire gene containing its coding region as well as its regulation region, obtained fragments were subcloned into an appropriate plasmid vector, which can be conveniently used for sequencing and construction of the entire gene of the enone reductase. In this invention, the insert fragments were subdoned into pUC18 vector. Nucleotide sequence can be determined by a well-known method such as dideoxy chain-termination method.

The isolated DNA sequence of the present invention may be used to identify and clone DNA encoding a polypeptide having enone reductase activity from other strains of different genera or species according to methods well known in the art.

The present invention also relates to a recombinant DNA, preferably a vector and/or plasmid comprising a sequence coding for enone reductase. The recombinant DNA vector and/or plasmid may comprise the regulatory regions such as promoters and terminators as well as open reading frames of a enone reductase gene. Methods which are well known to those skilled in the art may be used to construct expression vectors containing a nucleotide sequence encoding enone reductase and appropriate transcriptional and translational regulatory elements including all components which are necessary or advantageous for expression of the coding sequence of the nucleotide sequence. Specific initiation and termination signals may also be used to achieve more efficient translation of sequences encoding enone reductase. An isolated DNA sequence encoding enone reductase may be manipulated in a variety of ways to provide for expression of the polypeptide. Manipulation of the nucleotide sequence encoding enone reductase prior to its insertion into a vector may be desirable or necessary depending on the expression vector. The techniques for modifying nucleotide sequences utilizing cloning methods are well known in the art. A variety of expression vector/host systems may be utilized to contain and express sequences encoding enone reductase.

The present invention also provides the use of the recombinant DNA to transform a host organism. A convenient form of the recombinant DNA may be a vector. The host organism transformed with the recombinant DNA may be useful in the production of a polypeptide of enone reductase and also useful in the improvement of the production process of levodione. Thus, the present invention also provides such a transformed host cell (recombinant microorganism) and a polypeptide encoded by the recombinant DNA.

The present invention also provides a process for the production of the polypeptide encoded by the recombinant DNA, which comprises culturing the transformed host cell under the conditions suitable for the expression of the enzyme and recovery of the polypeptide from the cell culture. Cultivation of the recombinant microorganism can be carried out aerobically or anaerobically at pH values from 4.0 to 9.0, at a temperature in the range of from 10 to 60° C., for 15 minutes to 72 hours, preferably, at pH values from 5.0 to 8.0, at a temperature in the range of from 20 to 40° C. for 30 minutes to 48 hours. The enone reductase produced by the recombinant cell may be secreted or contained intra-celluarly depending on the sequence and/or the vector used. The enone reductase may then be isolated from the culture medium or the recombinant cell by conventional procedures.

The present invention further provides a process for the production of levodione, which comprises contacting ketoisophorone with the polypeptide enone reductase.

The enone reductase of the present invention catalyzes the reduction of ketoisophorone to levodione in the presence of a co-factor, NADH or NADPH, according to the following formula:

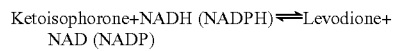

Ketoisophorone+NADH (NADPH) ⇌ Levodione+ NAD (NADP)

The reaction can be conducted in a solvent such as Tris-HCl buffer and phosphate buffer.

Preferable conditions for the reaction are pH values from 4.5 to 8.5, more preferably from 5.0 to 8.0, a temperature range of from 10 to 60° C., more preferably from 20 to 60° C., for a period of 5 minutes to 72 hours, more preferably for 15 minutes to 48 hours.

The present invention also provides a method for the biological production of levodione, which comprises contacting ketoisophorone with a recombinant microorganism as described above, including cultivation of the recombinant microorganism in the presence of ketoisophorone as a substrate, under conditions suitable for the production of levodione, and isolating the resulting levodione from the reaction mixture.

Either a growing or a resting cell culture or immobilized cells or a cell-free extract, or the like, of the recombinant microorganism may be used for the production of levodione.

The growing cell culture can be obtained by culturing the recombinant microorganism in a nutrient medium containing saccharides such as glucose or sucrose, alcohols, such as ethanol or glycerol, fatty acids, such as oleic acid and stearic acid or esters thereof, or oils, such as rapeseed oil or soybean oil, as carbon sources; ammonium sulfate, sodium nitrate, peptone, amino acids, corn steep liquor, bran, yeast extract and so on, as nitrogen sources; magnesium sulfate, sodium chloride, calcium carbonate, potassium monohydrogen phosphate, potassium dihydrogen phosphate, and so on, as inorganic salt sources; and malt extract, meat extract, and so on, as other nutrient sources. Cultivation of the recombinant microorganism can be carried out aerobically or anaerobically at pH values from 4.0 to 9.0, at a temperature in the range of from 10 to 60° C. for 15 minutes to 72 hours, preferably, at pH values from 5.0 to 8.0, at a temperature in the range of from 20 to 40° C. for 30 minutes to 48 hours. Appropriate mixing of the culture during the cultivation will be preferable for the cell growth or the reaction.

Using the growing cell culture thus obtained, a resting cell culture or immobilized cells or a cell-free extract may be prepared by any means generally known in the art.

Preferable conditions for the production of levodione are pH values from 4.0 to 9.0 and a temperature range of from 10 to 60° C. for a period of 15 minutes to 72 hours.

More preferable conditions for the production of levodione are pH values from 5.0 to 8.0 and a temperature range of from 20 to 60° C. for a period of 30 minutes to 48 hours.

The concentration of ketoisophorone in a reaction mixture can vary depending on other reaction conditions, but, in general, is between 0.1 g/l and 300 g/l, preferably between 1 g/l and 30 g/l.

Levodione produced enzymatically or biologically in a reaction mixture as described above may be extracted by an organic solvent such as ethyl acetate, n-hexane, toluene, or n-butyl. The extract may be analyzed by known method such as gas chromatography, high performance liquid chromatography, thin layer chromatography or paper chromatography, or the like. In case of gas chromatography, the following condition can be applied as an example: Column: ULBON HR-20M (Shinwa, Japan) 0.25 mm×30 m; Column temperature: 160° C. (constant); Injector temperature: 250° C.; Carrier gas: He (ca. 1 ml/min)

After the reaction, levodione in the reaction mixture may be recovered, for example, by extraction with a water-immiscible organic solvent, which readily solubilizes levodione, such as ethyl acetate, n-hexane, toluene, or n-butyl acetate. Further purification of levodione can be effected by concentrating the extract to directly crystallize levodione or by the combination of various kinds of chromatography, for example, thin layer chromatography, adsorption chromatography, ion-exchange chromatography, gel filtration chromatography or high performance liquid chromatography.

The following Examples further illustrate the present invention.

EXAMPLE 1

Partial Amino Acid Sequence of Enone Reductase of C. kefyr (C. macedoniensis) IFO 0960

The freeze-dried purified enone reductase (as described in European Patent Application No. 02003967.3 filed on Feb. 22, 2002) of C. kefyr was digested with lysyl endopeptidase, and the resulting digest was separated by the Smart system, i.e., one nmol of the purified enzyme was dissolved in 25 μl of 50 mM Tris-HCl buffer (pH 8.6) containing 8 M urea, and incubated at 37° C. for 1 hour. After this, 25 μl of 50 mM Tris-HCl buffer (pH 8.6) were added to make the concentration of urea 4 M. Then, 0.5 μl of 12 nmol/ml lysyl endopeptidase (Wako, Japan, 0.006 nmol, E/S=1/167) was added, and incubated at 30° C. for 6 hours. The resulting peptides were separated by the Smart system using the following conditions: Column: μRPC C2/C18 SC2.1/10 (Amersham Bioscience/Buckinghamshire, England); Flow rate: 100 μl/min; Liquid A: 0.1% TFA; Liquid B: 0.1% TFA+80% CH$_3$CN; Gradient: 100% A (0-15 min); 100% A→100% B (15-75 min); Column temperature: Room temperature; Detection: 214 nm, 280 nm.

The peptides (K-15, K-25.1, K-6.1, K-6.2, K30, K13.2, K-1.1, K-1.2, K-33, K-25.2, K-20, K-17, K-22, K-4.1, K-13.1, and K-9) were isolated, and the amino acid sequences of these peptides were analyzed with a protein sequencer, i.e. by automated Edman degradation with a model 491HT pulsed liquid protein sequencer (Applied Biosystems, Foster City, Calif.) to be Peptide K-15: SEQ ID NO: 3; PeptideK-25.1: SEQ ID NO: 4; Peptide K-6.1: SEQ ID NO: 5; Peptide K-6.2: SEQ ID NO: 6; Peptide K-30: SEQ ID NO: 7; Peptide K-13.2: SEQ ID NO: 8; Peptide K-1.1: SEQ ID NO: 9; Peptide K-1.2: SEQ ID NO: 10; Peptide K-33: SEQ ID NO: 11; Peptide K-25.2: SEQ ID NO: 12; Peptide K-20: SEQ ID NO: 13; Peptide K-17: SEQ ID NO: 14; Peptide K-22: SEQ ID NO: 15; Peptide K-4.1: SEQ ID NO: 16; Peptide K-13.1: SEQ ID NO: 17; and Peptide K-9: SEQ ID NO: 18.

The partial amino acid sequence obtained was compared with the sequences of proteins stored in the SWISS-PROT (release 37.0+/06-14, June 99), PIR (release 60.0, March 99), and PRF (release 99-05, May 99) protein databases. Sequence alignment was performed by using Blast (J. Mol. Biol., 215, 403-410, 1990) and Fasta (Proc. Natl. Acad. Sci. USA, 85, 2444-2448, 1988) programs. As a result, high homology with known Old Yellow Enzymes was found.

EXAMPLE 2

Preparation of Chromosomal DNA of C. kefyr (C. macedoniensis) IFO 0960

The cells of C. kefyr (C. macedoniensis) IFO 0960 were cultivated in 200 ml medium. Cells were collected by centrifugation and suspended in 10 ml TES buffer. 3 ml of 0.5 M EDTA, 0.5 ml of Zymolyase solution, and 0.5 ml of Proteinase K solution were added to the cell suspension. After incubation at 37° C. for 0.5 hour with gently mixing, 2 ml of 10% SDS was added and mixed. After addition of H$_2$O to make the volume 20 ml, 10 ml of TE-saturated phenol and 10 ml of chloroform were added and mixed. The upper layer was collected after centrifugation, the same volume of phenol/chloroform was added and mixed. After centrifugation, upper layer was collected and added with 0.1× volume of 3M sodium acetate and 2.5× volume of ethanol. Using a winding glass rod, DNA precipitate was collected, rinsed with 70%, 80%, and 90% ethanol, dried and resuspended in 5 ml of TE buffer containing 10 μl of 5 mg/ml RNase A. DNA was completely dissolved by gently mixing at 4° C. over night. 10 μl of 5 mg/ml RNase A were added again, and the DNA solution was incubated at 37° C. for 2 hours. After treatment with phenol/chloroform, water layer was recovered and the DNA was ethanol precipitated, followed by centrifugation. The pellet was resuspended in 50 ml of TE buffer. Concentration of thus obtained genomic DNA was 88 ng/μl.

EXAMPLE 3

Cloning of Partial Enone Reductase Gene of C. kefyr (C. macedoniensis) IFO 0960

Using the prepared genomic DNA as a template, a partial sequence for the enone reductase gene was obtained by degenerate PCR amplification using a thermal cycler (Perkin-Elmer Cetus Instruments, USA). The degenerate PCR primers were designed based on the partial amino acid sequences (K-15, K-13.1, and K-9) obtained in Example 1, and were as follows:

```
Sense 1
                                        (SEQ ID NO: 19)
     GlyAspThrAsnIlePheLysProIle
5'-GGIGATACIAATATATTTAAACCAAT-3'
         C    C T C G T
                    C      G
                           C Anti 2
                                        (SEQ ID NO: 20)
     GlyGluLysThrPheThrTyrPheThr
5'-CCTTCTTTAGTAAAIGTATAAAAIGT-3'
         C  T  G      G G
                G
                C
```

The PCR reaction (50 µl) was carried out using 176 ng of chromosomal DNA (obtained in Example 2) as a template, 150 pmol each of degenerate primer, 2.5 nmol each of dATP, dCTP, dGTP, and dTTP, 1.5 units of Ex Taq polymerase (Takara Shuzo, Kyoto, Japan), and 5 µl of EX Taq buffer (Takara Shuzo). The initial template denaturation step consisted of 4 min at 94° C. An amplification cycle of 1 min at 94° C., 1 min at 50° C., and 1.5 min at 72° C. was repeated for 35 times. After additional 10 min reaction at 72° C., a DNA fragment containing a partial enone reductase gene (approx. 1 kb) was amplified. This fragment was cloned on a sequencing vector, and DNA sequence was determined by the dideoxy chain-termination method. A Taq dye primer sequencing kit was used with an autosequencer (DNA Sequencer 373A, Applied Biosystems). The partial DNA sequence thus obtained for the enone reductase and deduced amino acid sequence are as illustrated in SEQ ID NO:21 and SEQ ID NO:22, respectively.

EXAMPLE 4

Cloning of Complete Enone Reductase Gene of *C. kefyr* (*C. niacedoniensis*) IFO 0960

The inverse PCR was used to clone both upstream and downstream sequence flanking the partial enone reductase DNA sequence obtained in Example 3.

1 µg of the genomic DNA of *C. kefyr* (*C. macedoniensis*) IFO 0960 (obtained in Example 2) was digested with 10 units of Nco I (Takara Shuzo, Kyoto, Japan) in 50 µl of K-buffer containing 0.01% BSA. After overnight reaction at 37° C., the reaction mixture was treated with phenol/chloroform, the water layer was recovered and the DNA was ethanol precipitated, followed by centrifugation. The DNA pellet was resuspended in 1 ml of T4 DNA ligase buffer containing 700 units of T4 DNA ligase (Takara Shuzo). After overnight reaction at 15° C., the reaction mixture was treated with phenol/chloroform, the water layer was recovered and the DNA was ethanol precipitated, followed by centrifugation. The DNA pellet was resuspended in TE buffer and used as a template for PCR. The PCR primers were designed based on the partial enone reductase gene sequence obtained in Example 3, and were as follows: IA1 (antisense primer for upstream region)=SEQ ID NO:23 and IS1 (sense primer for downstream region)=SEQ ID NO: 24.

The PCR reaction (50 µl) was carried out using 250 ng of the template DNA, 5 pmol each of primer, 2.5 nmol each of dATP, dCTP, dGTP, and dTTP, 2.5 units of Ex Taq polymerase (Takara Shuzo), and 5 µl of EX Taq buffer (Takara Shuzo). The initial template denaturation step consisted of 4 min at 94° C. An amplification cycle of 1 min at 94° C., 1 min at 60° C., and 4 min at 72° C. was repeated for 30 times. After additional 10 min reaction at 72° C., a DNA fragment (approx. 4 kb) containing the upstream and downstream sequence of the enone reductase gene was amplified. This fragment was cloned on a sequencing vector, and DNA sequence was determined.

By combining the thus obtained sequence with the partial enone reductase DNA sequence obtained in Example 3, an estimated entire gene sequence containing its coding region as well as its regulatory region such as a promoter or a terminator was obtained. The estimated entire DNA sequence thus obtained for the enone reductase is illustrated in SEQ ID NO: 25 containing the coding region as well as its flanking upstream and downstream region (estimated ORF is 148-1359).

Next, the actual entire sequence of the enone reductase gene containing its coding region as well as its flanking upstream and downstream region was obtained by PCR as follows.

The genomic DNA of *C. kefyr* (*C. macedoniensis*) IFO 0960 (obtained in Example 2) was used as a template. The PCR primers were designed based on the estimated enone reductase gene sequence obtained above (SEQ ID NO: 25), and are illustrated in SEQ ID NO: 26 (Sense) and SEQ ID NO: 27 (Antisense).

The PCR reaction (50 µl) was carried out using 900 ng of the template DNA, 10 pmol each of primer, 2.5 nmol each of dATP, dCTP, dGTP, and dTTP, 100 nmol of MgCl$_2$, 1.5 units of LA Taq polymerase (Takara Shuzo), and 5 µl of LA Taq buffer (Takara Shuzo). The initial template denaturation step consisted of 2 min at 94° C. An amplification cycle of 1 min at 94° C., 1 min at 60° C., and 1.5 min at 74° C. was repeated for 23 times. After additional 7 min reaction at 74° C., a DNA fragment (approx. 1.3 kb) containing the entire sequence of the enone reductase gene was amplified. This fragment was cloned on a sequencing vector, and the DNA sequence was determined.

The entire DNA sequence thus obtained for the enone reductase containing its coding region as well as its flanking upstream and downstream region is illustrated in SEQ ID NO:28 (ORF is 55-1266).

EXAMPLE 5

Expression of the Enone Reductase Gene and Levodione Production Using *E. coli* Having the Enone Reductase Gene of *C. kefyr*

A DNA fragment containing just the ORF of the enone reductase gene (1212 bp) was obtained by PCR amplification. The PCR was performed with primers, ExS (SEQ ID NO:29) and ExA (SEQ ID NO:30).

The vector carrying the entire sequence of the enone reductase gene (obtained in Example 4) was used as a template. The PCR reaction (50 µl) was carried out using 250 ng of the template DNA, 10 pmol each of primer, 2.5 nmol each of dATP, dCTP, dGTP, and dTTP, 1.5 units of Pyrobest DNA polymerase (Takara Shuzo), and 5 µl of Pyrobest buffer (Takara Shuzo). The initial template denaturation step consisted of 1 min at 94° C. An amplification cycle of 0.5 min at 94° C., 1 min at 60° C., and 1.5 min at 75° C. was repeated for 15 times. After additional 5 min reaction at 75° C., a DNA fragment (approx. 1.2 kb) containing just the ORF of enone reductase gene was amplified.

This amplified fragment of the enone reductase gene was cloned on a vector, pET101/D-TOPO, using a pET Directional TOPO® Expression Kits (Invitrogen Corporation, USA) according to an instruction manual prepared by the manufacturer. The vector carrying the enone reductase gene thus obtained (pET101/D-TOPO-ER) was introduced into E. coli BL21 (DE3), and several clones were selected for sequence analysis using an automatic sequence analyzer (DNA Sequencer 373A, Applied Biosystems). One of the clones, E. coli BL21 (DE3)[pET101/D-TOPO-ER], that showed completely the same sequence as the enone reductase sequence of C. kefyr was selected for further experiments. The strain, E. coli BL21 (DE3)[pET101/D-TOPO] was also prepared as a control.

Each of the strains, E. coli BL21 (DE3)[pET101/D-TOPO-ER] and E. coli BL21 (DE3)[pET101/D-TOPO], was inoculated into the M9 minimum medium (5 ml in tube) containing 0.05 mg/ml of ampicillin and 2% (W/V) of casamino acids (Difco laboratories, USA) and cultivated at 37° C. When the optical density at 610 nm reached 0.4, IPTG (isopropyl beta-D-thiogalactopyranoside) was added to the medium to make the concentration 0.01 mM and cultivation was continued for further 8-10 hours. Then the cells were collected by centrifugation, and a portion of the cells was used for SDS-PAGE analysis. As a result, an IPTG-induced protein band estimated as 45 kDa was observed only when the recombinant strain, E. coli BL21 (DE3)[pET101/D-TOPO-ER] was used.

The rest of the collected cells was resuspended into 2 ml of 100 mM potassium phosphate buffer (pH 7.0). The suspension was used for confirming an activity to produce levodione from ketoisophorone. This suspension was divided into two portions (1 ml each), and the reaction was started by adding 33 mM (final concentration, hereinafter abbreviated as f.c.) of ketoisophorone and 280 mM (f.c.) of D-glucose with or without 0.37 mM (f.c.) of $NAD^+$, 15 units/ml (f.c.) of glucose dehydrogenase. The reaction was carried out at 30° C. overnight. The reaction mixture was extracted with ethylacetate to recover levodione in the ethylacetate layer. The extract was analyzed by gas chromatography. As a result, levodione was detected only when the recombinant strain, E. coli BL2 1 (DE3)[pET101/D-TOPO-ER] was used.

The invention claimed is:

1. A process for the production of levodione, which comprises contacting ketoisophorone with an enzyme derived from *Candida* or *Zygosaccharomyces* which has enone reductase activity, wherein the enzyme is characterized by the following physico-chemical properties:
   (a) molecular mass: 61,300±5,000 Da as determined by gel filtration;
   (b) co-factor: NADPH and NADH;
   (c) substrate specificity: active on α,β-unsaturated ketones;
   (d) optimum temperature: 55-60° C. at pH 7.4; and
   (e) optimum pH: pH 4.5-8.5,
   in the presence of NADPH or NADH and isolating the resulting levodione from the reaction mixture.

2. The process of claim 1, wherein the ketoisophorone is contacted with the enzyme at pH values in the range of from 5.0 to 8.0 and at a temperature in the range of from 20 to 60° C. for 15 minutes to 48 hours.

3. The process of claim 1, wherein the enzyme is derived from *Candida*.

4. The process of claim 3, wherein the enzyme derived from *Candida* is derived from *Candida kefyr*.

5. The process of claim 4, wherein the enzyme derived from *Candida kefyr* is derived from *Candida kefyr* IFO 0960.

6. The process according to claim 1, wherein the enzyme is a polypeptide having the amino acid sequence shown in SEQ ID NO: 2 or is encoded by a polynucleotide that is at least 90% identical to a polynucleotide that encodes the polypeptide having the amino acid sequence shown in SEQ ID NO: 2 and has enone reductase activity.

7. The process according to claim 1, wherein the enzyme is a polypeptide having the amino acid sequence shown in SEQ ID NO: 2.

8. A process of claim 1, wherein ketoisophorone is contacted with the enzyme at pH values in the range of from 4.5 to 8.5 and at a temperature in the range of 10 to 60° C. for 5 minutes to 72 hours.

* * * * *